(12) United States Patent
Shraga

(10) Patent No.: US 8,192,750 B2
(45) Date of Patent: Jun. 5, 2012

(54) PHARMACEUTICAL COMPOSITION FOR THE TREATMENT OF OTOMYCOSIS

(76) Inventor: Shmuel Shraga, Jerusalem (IL)

( * ) Notice: Subject to any disclaimer, the term of this patent is extended or adjusted under 35 U.S.C. 154(b) by 5 days.

(21) Appl. No.: 12/304,502

(22) PCT Filed: Jun. 14, 2007

(86) PCT No.: PCT/IL2007/000724
§ 371 (c)(1),
(2), (4) Date: Dec. 12, 2008

(87) PCT Pub. No.: WO2007/144888
PCT Pub. Date: Dec. 21, 2007

(65) Prior Publication Data
US 2009/0202663 A1 Aug. 13, 2009

(30) Foreign Application Priority Data
Jun. 14, 2006 (IL) .......................................... 176303

(51) Int. Cl.
| | | |
|---|---|---|
| *A01N 25/34* | (2006.01) | |
| *A61F 9/02* | (2006.01) | |
| *A61K 36/00* | (2006.01) | |
| *A61K 31/56* | (2006.01) | |
| *A31K 36/53* | (2006.01) | |

(52) U.S. Cl. ......... 424/404; 424/437; 424/725; 514/169
(58) Field of Classification Search ........................ None
See application file for complete search history.

(56) References Cited

U.S. PATENT DOCUMENTS

| | | | | |
|---|---|---|---|---|
| 3,899,578 A | * | 8/1975 | Bird et al. ...................... | 514/462 |
| 4,298,604 A | * | 11/1981 | Hammell ...................... | 514/180 |
| 6,503,881 B2 | * | 1/2003 | Krieger et al. .................... | 514/2 |
| 2005/0158411 A1 | * | 7/2005 | Vail et al. ....................... | 424/747 |
| 2006/0003969 A1 | | 1/2006 | Manandhar et al. | |

OTHER PUBLICATIONS

Drugs-About.com: CLOTRISONE: Online, URL<http://drugs-about.com/drugs-c/clotrisone.html> pp. 1-2.*
Carson et al. Melaleuca Alternifolia (Tea Tree) OIL: A Review of Antimicrobial and Other Medicinal Properties: Clinical Microbiology Reviews, Jan. 2006, p. 50-62.*
International Preliminary Report on Patentability for PCT/IL2007/000724; mailed Mar. 17, 2009—4 pages.
Villars and Jones (1992) Br J Dermatol. 126(Suppl 39):61-9.
Wildfeuer et al., "In vitro evaluation of voriconazole against clinical isolates of yeasts, moulds and dermatophytes in comparison with itraconazole, ketoconazole, amphotericain B and griseofulvin", Mycoses 41, 1998, 309-319 (1988) (11 pages).
Bennett et al., "Oral Griseofulvin Remains the Treatment of Choice of Tinea Capitis in Children", Pediatric Dermatology 17(4), 304-309 (2000) (6 pages).
Fett et al., "An Unusual Case of Severe Grseofulvin-Alcohol Interaction", Annals of Emergency Medicine, 24(1):95-97 (Jul. 1994) (3 pages).
Katz et al., SCH 370 (Clotrimazole-Betamethasone Dipropionate) Cream in Patients with Tinea Cruris or Tinea Corpus, Therapeutics for the Clinician, 1994, 34: 183-186 and 188.
Gupta et al., Onychomycosis, Canadian Family Physician, 1997; 43: 299-305.
Fett et al. "An Unusual Case of Severe Griseofulvin-Alcohol Interaction", Annals of Emergency Medicine, 24(1):95-97 (Jul. 1994).
Ologe,—F-E, Nwabuisi,—C (2002) West AfrJ Med 21:34-36.
Savage, J.(1977) Br J Dermatol 97:107-108.

* cited by examiner

*Primary Examiner* — Patricia Leith
(74) *Attorney, Agent, or Firm* — Roach Brown McCarthy & Gruber, P.C.; Kevin D. McCarthy

(57) ABSTRACT

Disclosed is a composition comprising betamethasone, griseofulvin and tea tree oil, for use in the treatment of ear fungal infections, particularly otomycosis, particularly infections caused by *Aspergillus niger* or *Candida albicans*. The composition may be in the form of ointment, cream, gel or liquid, e.g. ear drops.

1 Claim, No Drawings

PHARMACEUTICAL COMPOSITION FOR THE TREATMENT OF OTOMYCOSIS

CLAIM OF PRIORITY

This application claims priority as a 371 of international of PCT/IL2007/000724, filed on Jun. 14, 2007; which claims priority to Israeli patent application serial number 176303, filed on Jun. 14, 2006.

FIELD OF THE INVENTION

The present invention relates to fungal infections. More specifically, the present invention relates to the treatment of ear infections of fungal origin by a new composition.

BACKGROUND OF THE INVENTION

All publications mentioned throughout this application are fully incorporated herein by reference, including all references cited therein.

Otomycosis is a fungal external ear canal infection that is caused by dermatophytes, especially *Aspergillus Niger* (80% to 90% of cases) and *Candida albicans* (second most common cause) [Ologe,-F-E, Nwabuisi,-C (2002) *West Afr J Med* 21:34-36]. The infection may be either acute or sub-acute and is characterized by inflammation, pruritus, and scaling, superficial epithelial exfoliation, mass of debris containing hyphae, suppuration and pain, which results in severe discomfort for the patient.

Until now, treatment has relied on a few drugs available in the market, which may be summarized as follows. Clotrisone® (Taro Pharmaceutical, Israel) is a combination of clotrimazole and betamethasone, is not specific for the treatment of *Aspergillus Niger*, but has been shown to be reliably effective in treating mild to moderate candidiasis, whereas the period of treatment is over 8 weeks. Similarly, Agisten® (Agis Pharmaceuticals Ltd., Bnei Brak, Israel) is also not specific for treatment of *Aspergillus niger*; it is reliably effective in treating mild to moderate candidiasis, with a period of treatment of more than 8 weeks as well.

Another drug is Pitrex (is used to designate antifungal preparations comprising as active ingredient tolnafatate—Tolnaftate 1%) (Teva Israel Pharmaceutical Ltd., Petah Tiqva, Israel) which is effective in treating superficial dermatophyte infections including corporis, cruris, pedis but not aspergillus infection. Dex-Otic (Teva Israel Pharmaceutical Ltd., Petah Tikya, Israel) is not effective against Aspergillus Niger and other fungal infections, but is effective against bacterial infection.

In addition, there is oral and topical treatment with Terbinafine (Lamisil®—is used to designate torbinafine hydrochloride, Novartis, Basel, Switzerland) for the treatment of systemic and topical mycosis (e.g., infections due to corporis, cruris, pedis, Alternaria, Curvularia, or Candida) [Villars and Jones (1992) Br J Dermatol. 126(Suppl 39):61-9].

Tevacutan cream (is used to designate Teva's antifungal cream comprising clotrimazole 1%, dexamethasone acetate 0.044%, and neomycin sulfate 0.645%) and Tevaderm his used to designate Teva's antifungal cream comprising diflucortolone valerate 0.1%, and isoconazole nitrate 1%) (Teva Israel Pharmaceutical Ltd., Petah Tikva, Israel) are also used against fungal infection but not for *Aspergillus* and *Candida*. However, these products are contraindicated to patients who have a history of tuberculosis, herpes simplex, varicella, vaxinia, external and canal perforation.

Griseofulvin is an antifungal agent first isolated from a *Penicillium* spp. in 1939. It is used to treat dermatophyte infections, e.g. skin infections such as jock itch, athlete's foot, and ringworm, as well as fungal infections of the scalp, fingernails, and toenails. Griseofulvin is effective after oral ingestion and reaches the skin and hair. Griseofulvin inhibits fungal mitosis by disrupting the mitotic spindle through interaction with polymerised microtubules. The compound is insoluble in water. The inventors have found that the solubility of griseofulvin was higher in admixture with high molecular weight substances, such as herbal agents (e.g. tea tree oil), but not in admixtures with saccharides or alcohol.

The present invention relates to a formulation comprised of betamethasone, griseofulvin and tea tree oil. The combination of the active agents, betamethasone, griseofulvin and tea tree oil provides an advantage over the use of each of the agents alone and over the formulations currently available in the market in that it can be assumed from the presented results that the combined effect of betamethasone and griseofulvin is the result of the additive role of the two drugs. Furthermore, the tree tea oil serves as a vehicle for griseofulvin, while also providing increased solubility for griseofulvin. Moreover, tea tree oil is rarely used as a monotherapy, but is more effective with other antifungal agents (Basset et al, 1990).

SUMMARY OF THE INVENTION

In a first aspect, the present invention provides the use of a mixture comprising betamethasone, griseofulvin and tea tree oil, in the preparation of a pharmaceutical composition for the treatment of ear fungal infections. The composition of the invention may further comprise pharmaceutically acceptable solvents, diluents and/or carriers.

In one preferred embodiment, said fungal infection is otomycosis, particularly a fungal infection caused by *Aspergillus niger* or *Candida albicans*, or by a combination of both, or even by other infectious fungae.

In one particular embodiment, betamethasone is present at a concentration between 0.01% and 1%, griseofulvin is present at a concentration between 1% and 40% and the tea tree oil is at a concentration of between 5% and 40%. Preferably, betamethasone is present at a concentration between 0.05% and 0.5%, griseofulvin is present at a concentration between 5% and 30% and the tea tree oil is at a concentration of between 10% and 30%. Most preferably, betamethasone is present at a concentration of 0.1%, griseofulvin is present at a concentration of 10-20% and the tea tree oil is at a concentration of between 15% and 20%.

In another embodiment, wherein said pharmaceutical composition is in the form of a cream, an ointment, or liquid, preferably a cream.

In further preferred embodiment, said composition is applied to the subject in need once or twice daily.

DETAILED DESCRIPTION OF THE INVENTION

The present inventor has developed a formulation intended for the topical treatment of fungal infections. This preparation contains antifungal agents such as griseofulvine, which were known mainly for oral use, and betamethasone, as well as an additional herbal component, tea tree oil (*Melaleuca alternifolia*).

Griseofulvine is an antibiotic first isolated from *Penicillium* spp. It is an anti-fungal drug usually administered orally and its specificity and efficacy have been proven over the years.

Betamethasone is a steroid, a synthetic glucocorticoid, known for its potent anti-inflammatory action, which also suppresses the immune response and is widely found in creams and in the treatment of fungal infection associated with inflammatory component.

The Tea Tree (*Melaleuca alternifolia*) is a member of the Myrtaceae family and is an indigenous species to Northern New South Wales, Australia. It has been known and used for centuries as a remedy, mainly for its anti-septic properties.

Thus, the present invention provides a pharmaceutical formulation (or composition) comprising betamethasone, griseofulvin and tea tree oil (Melaleuca oil), which may optionally further comprise pharmaceutically acceptable solvents, diluents and/or carriers, for the topical treatment of fungal infections.

More specifically, the present invention provides the use of a mixture comprising betamethasone, griseofulvin and tea tree oil in the preparation of a pharmaceutical composition for the treatment of ear fungal infections.

Although griseofulvin has been extensively used for the treatment of fungal infections, the combination of griseofulvin with betamethasone, especially for topical treatment, has not been used before (as mentioned, griseofulvin is insoluble in water).

Interestingly, some reports indicate that the use of corticosteroids in the treatment of fungal infections may lead to suppression of host inflammation leading to worsening or decreased cure rate. In particular, one report showed that betamethasone suppresses the alergenicity of griseofulvin [Savage, J. (1977) *Br J Dermatol* 97:107-108]. Nonetheless, as shown in the following Examples, use of the formulation of the invention in the treatment of ear fungal infections resulted in cure of the condition as soon as one week following beginning the treatment.

In another embodiment, the pharmaceutical formulation of the invention comprises betamethasone, at a concentration between 0.01% and 1%, griseofulvin, at a concentration between 1% and 40% and tea tree oil is at a concentration of between 5% and 40%. Preferably, betamethasone is present at a concentration between 0.05% and 0.5%, griseofulvin is present at a concentration between 5% and 30% and the tea tree oil is at a concentration of between 10% and 30%. Most preferably, betamethasone is present at a concentration of 0.1%, griseofulvin is present at a concentration of 10-20% and the tea tree oil is at a concentration of 15-20%.

In a further embodiment of the invention, the pharmaceutical formulation may be in the form of an ointment, a cream, a gel or liquid, as a spray or aerosol. A particular liquid form is useful as ear drops.

The therapeutic formulation or composition may also include, but it is not limited to, various additional agents, such as known antioxidants (e.g., vitamin E); buffering agents; lubricants (e.g., synthetic or natural beeswax); and other cosmetic agents (e.g., coloring agents, fragrances, oils, essential oils, moisturizers or drying agents). Thickening agents (e.g., polyvinylpyrrolidone, polyethylene glycol, carboxymethylcellulose, vaseline or glycerin) may also be added to the compositions.

In the therapeutic compositions of the present invention, the active agents are combined with a "carrier" which is physiologically compatible with the skin, membrane, or mucosal tissue of a human or animal to which it is topically administered. Specifically, in the preferred embodiment, the carrier is substantially inactive, with the exception of its intrinsic surfactant properties which are used in the production of a suspension of the active ingredients. The compositions may include other physiologically active constituents that do not interfere with the efficacy of the active agents in the composition. The carriers utilized in the therapeutic compositions of the present invention may be liquid or gel-based materials for use in liquid or gel formulations. The specific formulations depend, in part, upon the routes or modes of administration. Suitable liquid or gel-based carriers are well-known in the art (e.g., water, physiological salt solutions, urea, and the like). Preferably, water-based carriers have approximately neutral pH. Suitable carriers include aqueous and oleaginous carries such as, for example, white petrolatum, myristate, lanolin, mineral oil, fragrant or essential oil, nasturtium extract oil, sorbitan mono-oleate, detergents (e.g., polyoxyl stearate or sodium lauryl sulfate) and mixed with water to form a lotion, gel, cream or semi-solid composition. Other suitable carriers comprise water-in-oil or oil-in-water emulsions and mixtures of emulsifiers and emollients with solvents such as sucrose stearate, sucrose cocoate, sucrose distearate, mineral oil, and water. For example, emulsions containing water, glycerol stearate, glycerin, mineral oil, synthetic spermaceti, butylparaben, propylparaben and methylparaben are commercially available. Preservatives may also be included in the carrier including methylparaben and propylparaben. The composition may also include a plasticizer such as glycerol. The composition of the carrier can be varied so long as it does not interfere significantly with the pharmacological activity of the active ingredients of the therapeutic composition. Thus, any alcohol-based carriers are not used, since these have a contraindication with griseofulvin.

Hence, the pharmaceutical formulation of the invention is a remedy for topical use. As such, the formulation of the invention is for application directly to the affected area, i.e. in the external ear canal.

Generally, the active ingredients (the medications) of the topical formulation are mixed with or suspended in a vehicle, which is an inert carrier for the medications. The composition and consistency among topical formulations vary according to the vehicle, which determines the consistency of the product, which can go from thick and greasy to light and watery. Depending on the vehicle used, the formulation may be an ointment, a cream, a lotion, a solution or a gel. The vehicle in which the formulation of the invention is prepared, also aids in its absorption, and prevents the formation of plaques. Plaques are caused by the remnants of non-absorbed cream in the ear, which, together with cell membrane, may seal the ear canal.

The preparation of pharmaceutical formulations is well known in the art and has been described in many articles and textbooks, see e.g., Gennaro A. R. ed. (1990) *Remington's Pharmaceutical Sciences*, Mack Publishing Company, Easton, Pa., and especially pages 1521-1712 therein.

In a yet further embodiment, the pharmaceutical formulation of the invention is for use preferably once daily, but twice and even three times a day are also possible. The treatment is preferably for a minimum of seven days, but positive results may start being observed earlier than that.

Further, the present invention also provides a method of treatment of a fungal infection, wherein said method comprises applying the pharmaceutical formulation of the invention to a subject in need, on the area affected by the infection.

In said method of treatment, said subject is preferably a mammal. More preferably a human, but the treatment may also be applied to non-human mammals, such as house pets (cats, dogs, etc), as well as other domestic animals in need of such treatment. Said fungal infection is usually an external ear canal infection, often caused by *Aspergillus niger* and *Candida albicans*, alone or in combination.

Most importantly, *Candidiasis* and *Aspergillosis* are common fungal infections which especially affect subjects prone to the proliferation of opportunistic fungal infections. For example, subjects who are immunosuppressed, as in the case of patients suffering from cancer, AIDS, leukemia, or patients in need of organ transplant, or undertaking high doses of corticosteroid drugs, chemotherapy or other conditions that reduce the number of circulating leucocytes. Usually these subjects cannot receive non-specific, systemic anti-fungal drugs. The formulation presented herein is especially indicated for these patients, since it is intended for topical application. The formulation of the invention is also intended to prevent Aspergillosis related to pneumonia, which is most dangerous and fatal in these patients.

In the methods and compositions of the invention, the therapeutic effective amount, or dosage, is generally dependent on severity and responsiveness of the state of the disease to be treated, with the course of treatment lasting from several days to several weeks or months, or until cure or improvement are achieved. Optimal dosing schedules can be calculated from measurements of drug accumulation in the body of the patient and on basis of, e.g., the present examples. Persons of ordinary skill can easily determine optimum dosages, dosing methodologies and repetition rates. In general, dosage is calculated according to body weight, and may be given once or more daily, weekly or monthly. Persons of ordinary skill in the art can easily estimate repetition rates for dosing. Following successful treatment, it may be desirable to have the patient undergo maintenance therapy to prevent the recurrence of the disease state, wherein the composition of the invention may be administered in maintenance doses and frequencies.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Formulations:
1. Basic mixture
  0.1% Betamethasone
  20% Griseofulvin
  25% Vaseline
  15% Tea tree oil (Melaleuca oil)
  Water 200 ml
2. Ointment
  0.1% Betamethasone
  20% Griseofulvin
  20% Lanolin
  25% Vaseline
  15% Tea tree oil (Melaleuca oil)
  Water 200 ml
3. Cream
  0.1% Betamethasone
  10% Griseofulvin
  30% Lanolin
  20% Vaseline
  20% Tea tree oil (Melaleuca oil)
  Water 200 ml
4. Ear drops
  0.1% Betamethasone
  15% Griseofulvin
  9.5% Lanolin
  50% Glycerin
  10% Tea tree oil (Melaleuca oil)
  0.5% Lavender Oil
  Water (14.9%) up to 100 ml Briefly, 1 Kg of an ointment or cream forms of the formulation of the invention was prepared as follows. First, Griseofulvin (200 gr for an ointment and 100 gr for the cream form) and Betamethasone (1 gr for each cream or ointment) were added and mixed with the half indicated quantity of water. Lanolin (200 gr for ointment and 300 gr for cream) and Vaseline (250 gr for ointment and 200 gr for cream) were subsequently added and mixed gently. And finally, tea tree oil (200 ml) and the remaining quantity of water were added and mixed to form the formulation of the invention.

Example 1

Anti-Mycotic Properties of the Ointment in In Vitro Tests

Solubility of griseofulvin was tested in different solvents, and was found to be higher in mixtures with high molecular weight carriers such as herbal agents, but not with saccharides or alcohol.

A modified NCCLS M38-A test [National Committee for Clinical Laboratory Standards (2002) Reference method for broth dilution antifungal susceptibility testing of conidium forming filamentous fungi. Proposed standard M38-A. National Committee for Clinical Laboratory Standards, Wayne, Pa., USA], which is standard for moulds, was used. In vitro tests were done with the basic mixture, which does not contain lanolin. The mixture was kept at room temperature and thoroughly homogenized prior to each testing. All dilutions were done at a volume per volume basis.

In order to dissolve the mixture in water-based broth, the first dilution—at 10% v/v, was done in DMSO. Further dilutions were made with RPMI-1640, with final concentrations of 1%, 0.5%, 0.2%, 0.1%, 0.05%, 0.02% (all volume per volume), as controls tubes with pure RPMI-1640 and tubes with DMSO alone were used.

*Aspergillus fumigatus* (ATCC64026) was used as a reference strain, and always taken from the same refrigerated master stock. A 2 mm piece of agar with mould was cut from the master stock each time, and planted into an SDA plate. Plate was then incubated at 35° C. for 5-7 days, until widespread sporulation was visible. Spores were harvested by washing the plate with sterile saline containing Tween80, which was then transferred to sterile 10-mm test tubes and laid for 20 minutes. The supernatant, without the hyphae and other debris, was transferred to another tube and spore concentration was determined by placing a sample in a hemocytometer and counting under the microscope. Test tubes with the medium (RPMI-1640) were inoculated with *Aspergillus fumigatus* spores to a final concentration of $10^4$ spores per ml. Two tubes were not inoculated and kept as broth control. All tubes were incubated for 72 h at 35° C., with constant shaking at 200 rpm.

MIC (minimal inhibitory concentration) value was determined by visual examination of tubes for visible growth. MEC (minimal effective concentration) was determined by microscopic properties of the mould growing in the test tube, as compared to the RPMI only or DMSO control tubes. Microscopic examination was done on sampled material from tubes, using a Zeiss light phase contrast microscope under ×400 magnification.

About 80% inhibition of growth was seen in any of the test tubes (MIC>1%). Morphologic impact was noted in concentration of 0.1% v/v and above, evaluated by hyphae clamping. Hyphae were also swollen and crocked, and sporulation was scarcer as compared to the control samples. MEC was determined as 0.1% v/v.

Example 2

Clinical Studies

Clinical studies were performed in patients of the Department of Ear, Nose, Throat, Head and Neck Surgery of the Hadassah Ein Kerem University Hospital (Jerusalem, Israel), under the supervision of Prof. Joseph Elidan, and with the approval of the Helsinki committee of the Hadassah Medical Center and the Israeli Ministry of Health.

The cream approved by the Helsinki committee and used in the clinical trial consisted of:
  0.1% Betamethasone (as valerate)
  10% Griseofulvin
  37.5% Lanolin
  22% Vaseline
  15% Tea tree oil (Melaleuca oil)
  0.5% lavender oil
  14.9% Water
  In a total volume of 100 ml The ear drops approved by the Helsinki committee and used in the clinical trial consisted of:
  0.1% Betamethasone
  15% Griseofulvin
  9.5% Lanolin
  50% Glycerin
  10% Tea tree oil Melaleuca oil)
  0.5% Lavender Oil
  Water (14.9%) up to total volume of 100 ml Preliminary studies were performed in fifteen (ages 18-60) bearing fungal disease of the external ear canal (otomycosis), diagnosed clinically and mycologically, and the results are presented in Table 1.

With respect to the clinical diagnosis, the infection may be diagnosed as acute or sub-acute, and it is usually characterized by inflammation, pruritus, scaling, superficial epithelial exfoliation, mass of debris containing hyphae, suppuration and pain, which result in severe discomfort for the patient. The mycological diagnosis is done through microbiology lab culture.

TABLE 1

| Group | Age (n) | Duration of treatment (days) | Culture results |
|---|---|---|---|
| 1 | <50 (9)* | 7 | Neg. |
| 2 | >50 (4)** | 12 | Neg. |

*2 patients were diagnosed with both Aspergillys and *Candida*, while 4 patients had *Aspergillus* only.
**All patients with *Aspergillus* only.

Clinical and mycological cure was achieved in 13 patients. For the group age <50, culture was negative after 7 days, while for the group age >50, culture was negative following 12 days of treatment two patients stopped the treatment before achieving cure.

Clinical and mycological cure was also achieved in eight patients treated with ear drops in accordance with the invention.

A second clinical trial is being performed in a group of 50 patients,

The protocol for the clinical trial is as follows:

1. Patients are examined with an otoscope. If clinical analysis with the otoscope indicates a fungal infection, a fungal culture or scraping of external ear canal is taken by the attending physician, who also cleans the ear canal through suction.

2. The material is analyzed by microscopy.

3. The material is sent for culture at the Clinical Mycology laboratory of the Hadassah Ein Kerem University Hospital.

4. 0.5 g of cream is administered through a syringe into the ear canal.

5. The material is analyzed for the presence of fungal hyphea on 10% KOH.

6. The administration is continued for one week, 0.5 g of cream once a day daily, on the ear canal, using a cotton swab. This application may be performed by the patient (without the help of the attending physician).

7. After one week of administration the patient is evaluated by the attending physician.

8. A fungal culture or scraping of external ear canal is taken by the attending physician at the end of the treatment.

Preliminary results have demonstrated cure within one week of treatment, which is significantly more efficient that all the other treatments currently available in the market. In addition, the treatment did not show any side effects.

The invention claimed is:
1. An ear drop composition consisting essentially of:
  0.1% betamethasone;
  15% griseofulvin;
  10% tea tree oil;
  9.5% lanolin;
  0.5% lavender oil;
  50% glycerin; and
  water up to 100%.

* * * * *